United States Patent
Gamache

(10) Patent No.: US 9,248,028 B2
(45) Date of Patent: Feb. 2, 2016

(54) REMOVABLE, BONE-SECURING COVER PLATE FOR INTERVERTEBRAL FUSION CAGE

(75) Inventor: Thomas Gamache, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 413 days.

(21) Appl. No.: 13/235,106

(22) Filed: Sep. 16, 2011

(65) Prior Publication Data

US 2013/0073044 A1 Mar. 21, 2013

(51) Int. Cl.
*A61F 2/44* (2006.01)
*A61B 17/86* (2006.01)
*A61F 2/30* (2006.01)

(52) U.S. Cl.
CPC .................. *A61F 2/447* (2013.01); *A61F 2/442* (2013.01); *A61B 17/86* (2013.01); *A61F 2002/305* (2013.01); *A61F 2002/30439* (2013.01); *A61F 2002/30471* (2013.01); *A61F 2002/30482* (2013.01); *A61F 2002/30507* (2013.01); *A61F 2002/30579* (2013.01); *A61F 2002/30774* (2013.01); *A61F 2002/30779* (2013.01); *A61F 2002/30785* (2013.01); *A61F 2002/30787* (2013.01); *A61F 2002/30835* (2013.01); *A61F 2002/30904* (2013.01); *A61F 2002/4475* (2013.01); *A61F 2310/00017* (2013.01); *A61F 2310/00023* (2013.01); *A61F 2310/00029* (2013.01); *A61F 2310/0097* (2013.01);
(Continued)

(58) Field of Classification Search
CPC ........................................................ A61F 2/44
USPC .............................. 623/17.11–17.16; 606/289
See application file for complete search history.

(56) References Cited

U.S. PATENT DOCUMENTS

| 1,636,636 A | 7/1927 | Humble |
| 1,677,337 A | 7/1928 | Grove |
| 2,304,703 A | 12/1942 | O'Leary |

(Continued)

FOREIGN PATENT DOCUMENTS

| CN | 201244104 | 5/2009 |
| EP | 302719 | 2/1989 |

(Continued)

OTHER PUBLICATIONS

Allcock, "Polyphosphazenes", The Encyclopedia of Polymer Science, vol. 13, pp. 31-41, Wiley Intersciences, John Wiley & Sons, (1988).

(Continued)

*Primary Examiner* — Kevin T Truong
*Assistant Examiner* — Si Ming Ku

(57) ABSTRACT

A secondary cover plate that contacts a stand-alone fusion cage without rigidly connecting to the cage, and instead only docks against the cage (or passes through a fixation cage) and is secured into the adjacent bone. The secondary cover plate is the last item that would be added to the fixation cage construct and would at least partially cover the head of one or more angled screws. The secondary cover plate could slidably engage the fixation cage without permanently snapping into any features of the cage itself. The secondary cover plate would then be final positioned by advancing into one or more adjacent vertebral bodies. The secondary cover plate advancing step could be achieved by tapping it into place (into bone) or rotating it into place (into bone) so that it is finally secured into the bone.

4 Claims, 12 Drawing Sheets

(52) U.S. Cl.
CPC ............... *A61F2310/00407* (2013.01); *A61F 2310/00796* (2013.01); *A61F 2310/00976* (2013.01)

(56) References Cited

U.S. PATENT DOCUMENTS

| | | | |
|---|---|---|---|
| 4,105,034 A | 8/1978 | Shalaby |
| 4,130,639 A | 12/1978 | Shalaby |
| 4,140,678 A | 2/1979 | Shalaby |
| 4,141,087 A | 2/1979 | Shalaby |
| 4,205,399 A | 6/1980 | Shalaby |
| 4,208,511 A | 6/1980 | Shalaby |
| 4,904,261 A | 2/1990 | Dove |
| 4,955,908 A | 9/1990 | Frey |
| 5,041,113 A | 8/1991 | Biedermann |
| 5,352,231 A | 10/1994 | Brumfield |
| 5,391,170 A | 2/1995 | McGuire |
| 5,395,372 A | 3/1995 | Holt |
| 5,397,364 A | 3/1995 | Kozak |
| 5,443,514 A | 8/1995 | Steffee |
| 5,443,515 A | 8/1995 | Cohen |
| 5,464,407 A | 11/1995 | McGuire |
| 5,464,929 A | 11/1995 | Bezwada |
| 5,499,986 A | 3/1996 | Dimarco |
| 5,529,580 A | 6/1996 | Kusunoki |
| 5,534,031 A | 7/1996 | Matsuzaki |
| 5,595,751 A | 1/1997 | Bezwada |
| 5,597,579 A | 1/1997 | Bezwada |
| 5,607,687 A | 3/1997 | Bezwada |
| 5,618,552 A | 4/1997 | Bezwada |
| 5,620,698 A | 4/1997 | Bezwada |
| 5,645,598 A | 7/1997 | Brosnahan, III |
| 5,645,850 A | 7/1997 | Bezwada |
| 5,648,088 A | 7/1997 | Bezwada |
| 5,662,655 A | 9/1997 | Laboureau |
| 5,698,213 A | 12/1997 | Jamiolkowski |
| 5,700,583 A | 12/1997 | Jamiolkowski |
| 5,713,899 A | 2/1998 | Marnay |
| 5,776,196 A | 7/1998 | Matsuzaki |
| 5,779,707 A | 7/1998 | Bertholet |
| 5,785,713 A | 7/1998 | Jobe |
| 5,788,698 A | 8/1998 | Savornin |
| 5,797,918 A | 8/1998 | McGuire |
| 5,800,440 A | 9/1998 | Stead |
| 5,859,150 A | 1/1999 | Jamiolkowski |
| 5,888,223 A | 3/1999 | Bray, Jr. |
| 5,904,689 A | 5/1999 | Jonjic |
| 5,913,860 A | 6/1999 | Scholl |
| 6,049,026 A | 4/2000 | Muschler |
| 6,056,749 A | 5/2000 | Kuslich |
| 6,066,175 A | 5/2000 | Henderson |
| 6,093,205 A | 7/2000 | McLeod |
| 6,099,531 A | 8/2000 | Bonutti |
| 6,120,503 A | 9/2000 | Michelson |
| 6,156,037 A | 12/2000 | LeHuec |
| 6,159,211 A | 12/2000 | Boriani |
| 6,200,306 B1 | 3/2001 | Klostermeyer |
| 6,206,922 B1 | 3/2001 | Zdeblick |
| 6,231,610 B1 | 5/2001 | Geisler |
| 6,235,059 B1 | 5/2001 | Benezech |
| 6,306,170 B2 | 10/2001 | Ray |
| 6,330,845 B1 | 12/2001 | Meulink |
| 6,336,928 B1 | 1/2002 | Guerin |
| 6,342,055 B1 | 1/2002 | Eisermann |
| 6,342,074 B1 | 1/2002 | Simpson |
| 6,364,880 B1 | 4/2002 | Michelson |
| 6,375,462 B2 | 4/2002 | Holweg et al. |
| 6,387,130 B1 | 5/2002 | Stone |
| 6,406,478 B1 * | 6/2002 | Kuo ........................ 606/71 |
| 6,423,063 B1 | 7/2002 | Bonutti |
| 6,428,575 B2 | 8/2002 | Koo |
| 6,432,106 B1 | 8/2002 | Fraser |
| 6,447,546 B1 | 9/2002 | Bramlet |
| 6,461,359 B1 | 10/2002 | Tribus |
| 6,471,724 B2 | 10/2002 | Zdeblick |
| 6,558,387 B2 | 5/2003 | Errico |
| 6,558,423 B1 | 5/2003 | Michelson |
| 6,562,073 B2 | 5/2003 | Foley |
| 6,565,570 B2 | 5/2003 | Sterett |
| 6,572,619 B2 | 6/2003 | Santilli |
| 6,579,290 B1 | 6/2003 | Hardcastle |
| 6,602,257 B1 | 8/2003 | Thramann |
| 6,629,998 B1 | 10/2003 | Lin |
| 6,682,563 B2 | 1/2004 | Scharf |
| 6,730,125 B1 | 5/2004 | Lin |
| 6,730,127 B2 | 5/2004 | Michelson |
| 6,733,531 B1 | 5/2004 | Trieu |
| 6,736,850 B2 | 5/2004 | Davis |
| 6,770,096 B2 | 8/2004 | Bolger |
| 6,773,437 B2 | 8/2004 | Ogilvie |
| 6,805,714 B2 | 10/2004 | Sutcliffe |
| 6,824,564 B2 | 11/2004 | Crozet |
| 6,837,905 B1 | 1/2005 | Lieberman |
| 6,849,093 B2 | 2/2005 | Michelson |
| 6,890,335 B2 | 5/2005 | Grabowski |
| 6,890,355 B2 | 5/2005 | Michelson |
| 6,945,973 B2 | 9/2005 | Bray |
| 6,972,019 B2 | 12/2005 | Michelson |
| 6,974,479 B2 | 12/2005 | Trieu |
| 6,984,234 B2 | 1/2006 | Bray |
| 7,001,385 B2 | 2/2006 | Bonutti |
| 7,033,394 B2 | 4/2006 | Michelson |
| 7,041,135 B2 | 5/2006 | Michelson |
| 7,063,491 B2 | 6/2006 | French |
| 7,077,864 B2 | 7/2006 | Byrd, III |
| 7,112,222 B2 | 9/2006 | Fraser |
| 7,112,223 B2 | 9/2006 | Davis |
| 7,135,024 B2 | 11/2006 | Cook |
| 7,135,043 B2 | 11/2006 | Nakahara |
| 7,163,561 B2 | 1/2007 | Michelson |
| 7,172,627 B2 | 2/2007 | Fiere |
| 7,226,482 B2 | 6/2007 | Messerli |
| 7,232,463 B2 | 6/2007 | Falahee |
| 7,232,464 B2 | 6/2007 | Mathieu |
| 7,238,203 B2 | 7/2007 | Bagga |
| 7,238,206 B2 | 7/2007 | Lange |
| 7,255,698 B2 | 8/2007 | Michelson |
| 7,276,081 B1 | 10/2007 | Coates |
| 7,288,094 B2 | 10/2007 | Lindemann |
| 7,288,114 B2 | 10/2007 | Lange |
| 7,306,605 B2 | 12/2007 | Ross |
| 7,309,358 B2 | 12/2007 | Berry |
| 7,311,734 B2 | 12/2007 | Van Hoeck |
| 7,316,714 B2 | 1/2008 | Gordon |
| 7,323,011 B2 | 1/2008 | Shepard |
| 7,326,248 B2 | 2/2008 | Michelson |
| 7,341,587 B2 | 3/2008 | Molz, IV |
| 7,354,452 B2 | 4/2008 | Foley |
| 7,361,193 B2 | 4/2008 | Frey |
| 7,435,262 B2 | 10/2008 | Michelson |
| 7,442,209 B2 | 10/2008 | Michelson |
| 7,452,370 B2 | 11/2008 | Anderson |
| 7,491,237 B2 | 2/2009 | Randall |
| 7,527,641 B2 * | 5/2009 | Suh ........................ 606/289 |
| 7,594,931 B2 | 9/2009 | Louis |
| 7,594,932 B2 | 9/2009 | Aferzon |
| 7,601,173 B2 | 10/2009 | Messerli |
| 7,608,062 B2 | 10/2009 | Sweeney |
| 7,618,456 B2 | 11/2009 | Mathieu |
| 7,628,816 B2 | 12/2009 | Magerl |
| 7,658,766 B2 | 2/2010 | Melkent |
| 7,662,182 B2 | 2/2010 | Zubok |
| 7,674,279 B2 | 3/2010 | Johnson |
| 7,726,002 B2 | 6/2010 | Shimp |
| 7,794,502 B2 | 9/2010 | Michelson |
| 7,875,076 B2 | 1/2011 | Mathieu |
| 8,343,219 B2 | 1/2013 | Allain |
| 8,460,385 B1 | 6/2013 | Wensel |
| 8,617,245 B2 | 12/2013 | Brett |
| 8,932,359 B2 | 1/2015 | Brett |
| 9,005,295 B2 | 4/2015 | Kueenzi et al. |
| 2002/0029044 A1 | 3/2002 | Monassevitch |
| 2002/0029082 A1 | 3/2002 | Muhanna |
| 2002/0095155 A1 | 7/2002 | Michelson |

(56) References Cited

U.S. PATENT DOCUMENTS

| Publication No. | Date | Name | Ref |
|---|---|---|---|
| 2003/0050645 A1 | 3/2003 | Parker | |
| 2003/0100949 A1* | 5/2003 | Michelson | 623/17.11 |
| 2003/0125739 A1 | 7/2003 | Bagga | |
| 2003/0153975 A1 | 8/2003 | Byrd | |
| 2003/0158555 A1 | 8/2003 | Sanders | |
| 2003/0187506 A1 | 10/2003 | Ross | |
| 2003/0195632 A1 | 10/2003 | Foley | |
| 2004/0024464 A1 | 2/2004 | Errico | |
| 2004/0034430 A1 | 2/2004 | Falahee | |
| 2004/0092929 A1 | 5/2004 | Zindrick | |
| 2004/0111089 A1 | 6/2004 | Stevens | |
| 2004/0127902 A1 | 7/2004 | Suzuki | |
| 2004/0127990 A1 | 7/2004 | Bartish | |
| 2004/0153072 A1 | 8/2004 | Bonutti | |
| 2004/0199253 A1 | 10/2004 | Link | |
| 2004/0199254 A1 | 10/2004 | Louis | |
| 2004/0210219 A1 | 10/2004 | Bray | |
| 2004/0249377 A1 | 12/2004 | Kaes | |
| 2004/0260286 A1 | 12/2004 | Ferree | |
| 2005/0033433 A1 | 2/2005 | Michelson | |
| 2005/0038513 A1 | 2/2005 | Michelson | |
| 2005/0065608 A1 | 3/2005 | Michelson | |
| 2005/0071006 A1 | 3/2005 | Kirschman | |
| 2005/0071008 A1 | 3/2005 | Kirschman | |
| 2005/0085913 A1 | 4/2005 | Fraser | |
| 2005/0143749 A1 | 6/2005 | Zalenski | |
| 2005/0149192 A1 | 7/2005 | Zucherman | |
| 2005/0149193 A1 | 7/2005 | Zucherman | |
| 2005/0159813 A1 | 7/2005 | Molz | |
| 2006/0030851 A1 | 2/2006 | Bray | |
| 2006/0058801 A1 | 3/2006 | Schlienger | |
| 2006/0079961 A1 | 4/2006 | Michelson | |
| 2006/0085071 A1 | 4/2006 | Lechmann | |
| 2006/0129424 A1 | 6/2006 | Chan | |
| 2006/0142765 A9 | 6/2006 | Dixon | |
| 2006/0142863 A1 | 6/2006 | Fraser | |
| 2006/0235403 A1 | 10/2006 | Blain | |
| 2006/0235535 A1 | 10/2006 | Ferree | |
| 2006/0293753 A1 | 12/2006 | Thramann | |
| 2007/0106384 A1 | 5/2007 | Bray | |
| 2007/0106388 A1* | 5/2007 | Michelson | 623/17.16 |
| 2007/0129804 A1 | 6/2007 | Bentley | |
| 2007/0162138 A1 | 7/2007 | Heinz | |
| 2007/0219635 A1 | 9/2007 | Mathieu | |
| 2007/0233253 A1 | 10/2007 | Bray | |
| 2007/0233263 A1 | 10/2007 | Melkent | |
| 2007/0250167 A1 | 10/2007 | Bray | |
| 2007/0255416 A1 | 11/2007 | Melkent | |
| 2007/0265631 A1 | 11/2007 | Fox | |
| 2007/0270965 A1 | 11/2007 | Ferguson | |
| 2007/0293948 A1 | 12/2007 | Bagga | |
| 2008/0015694 A1 | 1/2008 | Tribus | |
| 2008/0027550 A1 | 1/2008 | Link | |
| 2008/0033440 A1 | 2/2008 | Moskowitz | |
| 2008/0065219 A1 | 3/2008 | Dye | |
| 2008/0077247 A1 | 3/2008 | Murillo | |
| 2008/0082173 A1 | 4/2008 | Delurio | |
| 2008/0097436 A1 | 4/2008 | Culbert | |
| 2008/0103598 A1 | 5/2008 | Trudeau | |
| 2008/0125865 A1 | 5/2008 | Abdelgany | |
| 2008/0132949 A1 | 6/2008 | Aferzon | |
| 2008/0132958 A1 | 6/2008 | Pech | |
| 2008/0133012 A1 | 6/2008 | McGuckin | |
| 2008/0161925 A1 | 7/2008 | Brittan | |
| 2008/0167666 A1 | 7/2008 | Fiere | |
| 2008/0177307 A1 | 7/2008 | Moskowitz | |
| 2008/0183293 A1* | 7/2008 | Parry et al. | 623/17.11 |
| 2008/0243136 A1 | 10/2008 | Prager | |
| 2008/0249569 A1* | 10/2008 | Waugh et al. | 606/249 |
| 2008/0249575 A1 | 10/2008 | Waugh | |
| 2008/0249625 A1 | 10/2008 | Waugh | |
| 2008/0255620 A1 | 10/2008 | Strauss | |
| 2008/0269806 A1 | 10/2008 | Zhang | |
| 2008/0281425 A1 | 11/2008 | Thalgott | |
| 2008/0294262 A1 | 11/2008 | Levieux | |
| 2008/0300634 A1 | 12/2008 | Gray | |
| 2008/0306596 A1 | 12/2008 | Jones | |
| 2008/0306598 A1 | 12/2008 | Hansen | |
| 2008/0312698 A1 | 12/2008 | Bergeron | |
| 2008/0312742 A1 | 12/2008 | Abernathie | |
| 2009/0030421 A1 | 1/2009 | Hawkins | |
| 2009/0030519 A1 | 1/2009 | Falahee | |
| 2009/0030520 A1 | 1/2009 | Biedermann | |
| 2009/0062921 A1 | 3/2009 | Michelson | |
| 2009/0088849 A1 | 4/2009 | Armstrong | |
| 2009/0099554 A1 | 4/2009 | Forster | |
| 2009/0105771 A1 | 4/2009 | Lei | |
| 2009/0105774 A1 | 4/2009 | Jones | |
| 2009/0105830 A1 | 4/2009 | Jones | |
| 2009/0105831 A1 | 4/2009 | Jones | |
| 2009/0125028 A1 | 5/2009 | Teisen | |
| 2009/0131988 A1* | 5/2009 | Bush et al. | 606/280 |
| 2009/0132054 A1* | 5/2009 | Zeegers | 623/17.16 |
| 2009/0143859 A1 | 6/2009 | McClellan, III | |
| 2009/0164020 A1 | 6/2009 | Janowski | |
| 2009/0182430 A1 | 7/2009 | Tyber | |
| 2009/0192549 A1 | 7/2009 | Sanders | |
| 2009/0192613 A1 | 7/2009 | Wing | |
| 2009/0192615 A1 | 7/2009 | Tyber | |
| 2009/0198245 A1 | 8/2009 | Phan | |
| 2009/0198287 A1 | 8/2009 | Chiu | |
| 2009/0210062 A1 | 8/2009 | Thalgott | |
| 2009/0210064 A1 | 8/2009 | Lechmann | |
| 2009/0265007 A1 | 10/2009 | Colleran | |
| 2009/0287251 A1 | 11/2009 | Bae | |
| 2010/0004747 A1 | 1/2010 | Lin | |
| 2010/0023128 A1 | 1/2010 | Malberg | |
| 2010/0036496 A1 | 2/2010 | Yu | |
| 2010/0057206 A1 | 3/2010 | Duffield | |
| 2010/0087925 A1 | 4/2010 | Kostuik | |
| 2010/0106249 A1 | 4/2010 | Tyber | |
| 2010/0145457 A1 | 6/2010 | Felt | |
| 2010/0145459 A1 | 6/2010 | McDonough | |
| 2010/0145460 A1 | 6/2010 | McDonough | |
| 2010/0185289 A1 | 7/2010 | Kirwan | |
| 2010/0204739 A1 | 8/2010 | Bae et al. | |
| 2010/0217325 A1 | 8/2010 | Hochschuler | |
| 2010/0217393 A1 | 8/2010 | Theofilos | |
| 2010/0249935 A1 | 9/2010 | Slivka | |
| 2010/0286777 A1 | 11/2010 | Errico | |
| 2010/0305704 A1 | 12/2010 | Messerli | |
| 2010/0312345 A1 | 12/2010 | Duffield | |
| 2011/0009966 A1 | 1/2011 | Michelson | |
| 2011/0015675 A1 | 1/2011 | Howard | |
| 2011/0082555 A1 | 4/2011 | Martz | |
| 2011/0098747 A1 | 4/2011 | Donner | |
| 2011/0144703 A1 | 6/2011 | Krause | |
| 2011/0208311 A1* | 8/2011 | Janowski | 623/17.16 |
| 2011/0230971 A1 | 9/2011 | Donner | |
| 2011/0319896 A1 | 12/2011 | Papenfuss | |
| 2011/0319998 A1 | 12/2011 | O'Neil | |
| 2012/0078371 A1 | 3/2012 | Gamache | |
| 2012/0078372 A1 | 3/2012 | Gamache | |
| 2012/0078373 A1 | 3/2012 | Gamache | |
| 2012/0150301 A1 | 6/2012 | Gamache | |
| 2012/0197401 A1 | 8/2012 | Duncan | |
| 2012/0203230 A1 | 8/2012 | Adams | |
| 2013/0073044 A1 | 3/2013 | Gamache | |
| 2014/0135930 A1 | 5/2014 | Georges | |

FOREIGN PATENT DOCUMENTS

| | | |
|---|---|---|
| EP | 974319 | 1/2000 |
| EP | 1103236 | 5/2001 |
| EP | 1391189 | 2/2004 |
| EP | 1470803 | 10/2004 |
| EP | 1683490 | 7/2006 |
| EP | 1774926 | 4/2007 |
| EP | 1847240 | 10/2007 |
| GB | 2220729 | 1/1990 |
| GB | 2457673 | 8/2009 |
| WO | WO 9423654 A1 | 10/1994 |
| WO | WO 9720526 A1 | 6/1997 |
| WO | WO 9737620 A1 | 10/1997 |

(56) References Cited

FOREIGN PATENT DOCUMENTS

| | | |
|---|---|---|
| WO | WO 9804217 A1 | 2/1998 |
| WO | WO 9927864 A2 | 6/1999 |
| WO | WO 9938463 A2 | 8/1999 |
| WO | WO 9952473 A1 | 10/1999 |
| WO | WO 9963914 A1 | 12/1999 |
| WO | WO 0101894 A1 | 1/2001 |
| WO | 0108864 | 2/2001 |
| WO | WO 0213732 A2 | 2/2002 |
| WO | WO 02080819 A1 | 10/2002 |
| WO | WO 03005938 A1 | 1/2003 |
| WO | WO 03005939 A2 | 1/2003 |
| WO | WO 03057088 A1 | 7/2003 |
| WO | WO 03070128 A1 | 8/2003 |
| WO | WO 03090650 A1 | 11/2003 |
| WO | WO 2004069106 A1 | 8/2004 |
| WO | WO 2004093749 A1 | 11/2004 |
| WO | WO 2005020861 A1 | 3/2005 |
| WO | WO 2006084057 A1 | 8/2006 |
| WO | WO 2007003785 A1 | 1/2007 |
| WO | WO 2007065993 A2 | 6/2007 |
| WO | WO 2007070751 A1 | 6/2007 |
| WO | WO 2007079021 A2 | 7/2007 |
| WO | WO 2007098288 A2 | 8/2007 |
| WO | WO 2007118856 A1 | 10/2007 |
| WO | WO 2007079021 A3 | 11/2007 |
| WO | WO 2007065993 A3 | 12/2007 |
| WO | WO 2008149223 A2 | 12/2008 |
| WO | WO 2009064644 A1 | 5/2009 |
| WO | 2009091775 | 9/2009 |
| WO | WO 2010028045 A1 | 3/2010 |
| WO | 2010092893 | 8/2010 |
| WO | 2010121028 | 12/2010 |
| WO | WO 2010099239 A3 | 1/2011 |
| WO | 2013018062 | 2/2013 |

OTHER PUBLICATIONS

Cain, "New Stand-Alone Anterior Lumbar Interbody Fusion Device: Bioemechanical Comparison with Established Fixation Techniques", Spine, vol. 30, No. 23, pp. 2631-2636, 2005, Lippincott Williams & Wilkins Inc.

Cohn and Younes, "Biodegradable PEO/PLA Block Copolymers", Journal of Biomaterials Research, 1988, vol. 22, pp. 993-1009.

Cohn, "Polymer Preprints", ACS Division of Polymer Chemistry, vol. 30(1), 1989, p. 498, (e.g. PEO/PLA).

Gercek, "Subsidence of Stand-Alone Cervical Cages in Anterior Interbody Fusion: Warning", Eur Spine J., vol. 12, pp. 513-516, 2003, Springer-Verlag.

Heller, "Poly(Ortho Esters)", Handbook of Biodegradable Polymers, edited by Domb, et al, Hardwood Academic Press, pp. 99-118, 1997.

Humphries, "Anterior Fusion of the Lumbar Spine Using An Internal Fixative Device", Surgical Forum, vol. IX, pp. 770-773, American College of Surgeons, 1959, Chicago Illinois.

Kandziora, "Biomechanical Comparison of Cervical Spine Interbody Fusion Cages", Spine, vol. 26, No. 17, pp. 1850-1857, 2001, Lippincott Williams & Wilkins, Inc.

Kemnitzer and Kohn, "Degradable Polymers Derived From the Amino Acid L-Tyrosine", The Handbook of Biodegradable Polymers, edited by Domb, et. al., Hardwood Academic Press, 1997, pp. 251-272.

Oxland, "A Comparative Biomechanical Investigation of Anterior Lumbar Interbody Cages: Central and Bilateral Approaches", The Journal of Bone and Joint Surgery, pp. 383-393, vol. 82A, No. 3, Mar. 2000.

Pavlov, "Good Outcome and Restoration of Lordosis After Anterior Lumbar Interbody Fusion With Additional Posterior Fixation", Spine, vol. 29, No. 17, pp. 1893-1900, 2004, Lippincott Williams & Wilkins.

Samandouras, "A New Anterior Cervical Instrumentation System Combining an Intradiscal Cage With an Integrated Plate", Spine, vol. 26, No. 10, pp. 1188-1192, 2001, Lippincott Williams and Watkins, Inc.

Vandorpe, "Biodegradable Polyphosphazenes for Biomeidcal Applications", The Handbook of Biodegradable Polymers, edited by Domb, et al, Hardwood Academic Press, 1997, pp. 161-182.

Pederson, "Thermal Assembly of A Biomimetic Mineral/Collagen Composite", Biomaterials, 2003, vol. 2, pp. 4881-4890, Elsevier.

Unpublished U.S. Appl. No. 13/673,061, filed Nov. 9, 2012.

* cited by examiner

REMOVABLE, BONE-SECURING COVER PLATE FOR INTERVERTEBRAL FUSION CAGE

BACKGROUND OF THE INVENTION

A stand-alone fusion cage is a fusion cage that has at least one angled hole in its anterior face for receiving a bone screw that passes through the cage an into an adjacent vertebral body. There are numerous conventional embodiments of these cages that capture the angled bone-engaging screw so as to ensure that the screw does not back out of the cage. Some of the known anti-backout mechanisms include: assembled rotating cover plates, cams, bushings, expanding screws, set screws and secondary cover plates that either snap onto the cage itself or are docked to the cage and secured to the cage faceplate using additional hardware such as a screw. These secondary cover plates can fully or partially cover the most proximal (anterior) portion of the screw head and would in theory prevent any screw backouts.

The following references are pertinent to the field of stand-alone cages: US 2008-0027550 (Link); US2010-0057206; U.S. Pat. No. 6,730,127; US2009-0088849; US2010-0145459; U.S. Pat. No. 7,662,182; U.S. Pat. No. 6,972,019; US2008-0249569; US2009-0105831; U.S. Pat. No. 7,306,605; U.S. Pat. No. 7,288,094; US2010-0312345; US2010-0286777; U.S. Pat. No. 6,945,973; US2010-0106249; U.S. Pat. No. 6,849,093; U.S. Pat. No. 6,984,234; US2009-0105830; US2009-0210062; U.S. Pat. No. 7,452,370; U.S. Pat. No. 6,558,423; U.S. Pat. No. 6,890,335; and U.S. Pat. No. 6,629,998.

SUMMARY OF THE INVENTION

The present invention relates to a secondary cover plate that engages a stand-alone intervertebral fusion cage without rigidly connecting to the cage. Rather, the cover plate of the present invention only docks against or passes through the cage and is secured into the adjacent bone.

The secondary cover plate of the present invention is typically the last component of the intervertebral fusion assembly that is inserted into the disc space. Typically, its primary function is to at least partially cover the head of one or more angled screws.

In some embodiments, the secondary cover plate of the present invention slidably engages the fixation cage without permanently snapping into any features of the cage component. In other embodiments, the secondary cover plate threadably engages the cage without permanently snapping into any features of the cage.

After this removable engagement, the secondary cover plate is then secured into its final position by advancing into one or more adjacent vertebral bodies. This advancing step may be achieved by tapping its bone-securement features into the adjacent bones or rotating these bone securement features into the adjacent bone, so that the cover plate is finally secured into the bone.

Therefore, in accordance with the present invention, there is provided an assembly comprising:
a) an intervertebral fusion cage positionable between adjacent vertebral bodies, the cage having an anterior face having a pair of anchor holes extending therethrough,
b) bone anchors received in the anchor holes, each anchor having a proximal head,
c) a cover plate having:
   i) a base portion having an anterior face and a posterior face,
   ii) opposed bone-securing features extending from the base portion,
wherein the cover plate is removably connected to the cage.

DETAILED DESCRIPTION OF THE INVENTION

Figure 3:
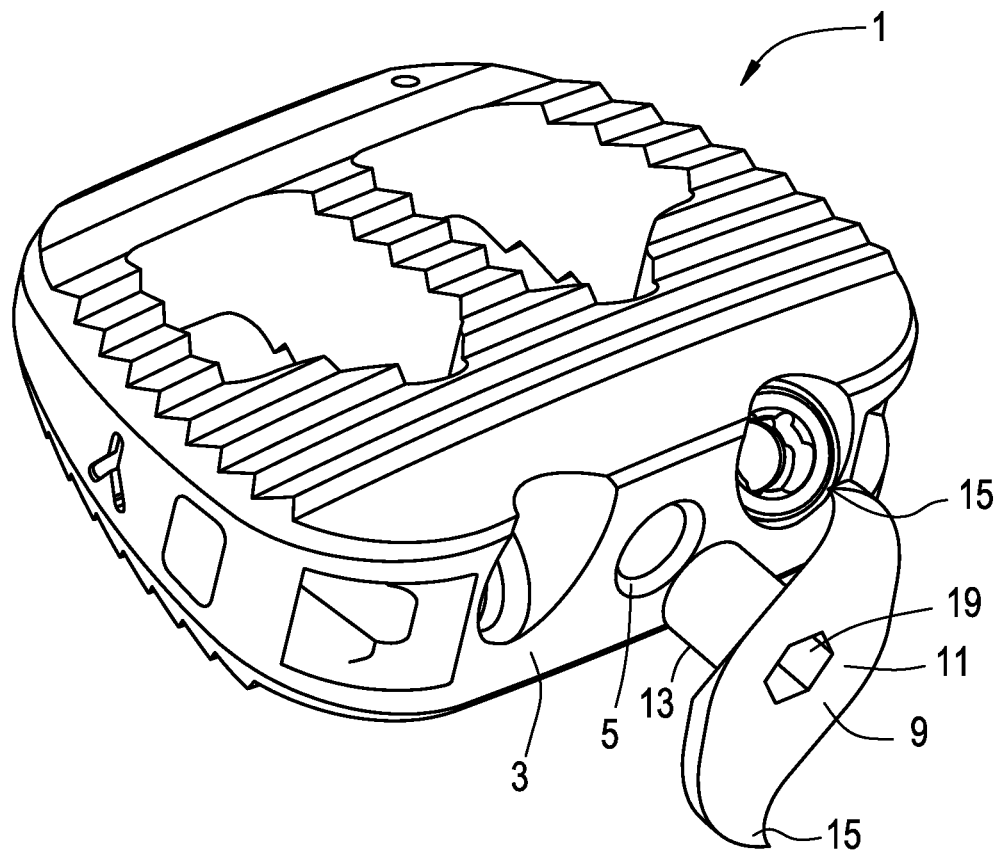
FIG. 3 discloses an exploded version of a second embodiment of the present invention (without screws) having a smooth post, wherein the bone-securing features are in deployed position.

Now referring to FIGS. 1A-B, 2A-B, 3 and 6, there is provided an assembly comprising:
a) an intervertebral fusion cage 1 positionable between adjacent vertebral bodies, the cage having an anterior face 3 having a receptacle 5 and a pair of anchor holes 901, and
b) a cover plate 7 having:
   i) a base portion 9 having an anterior face 11 and a posterior face (not shown),
   ii) a post 13 extending from the posterior face of the base portion and removably engaged in the receptacle of the cage, and
   iii) opposed bone-securing features 15 for engaging the adjacent vertebral bodies
c) bone anchors 903 received in the anchor holes, each anchor having a proximal head 905, and In some embodiments, as in FIG. 3, the shaft and receptacle each have mating circular transverse cross-sections so that the shaft is rotatable with the receptacle.

Figure 1A:
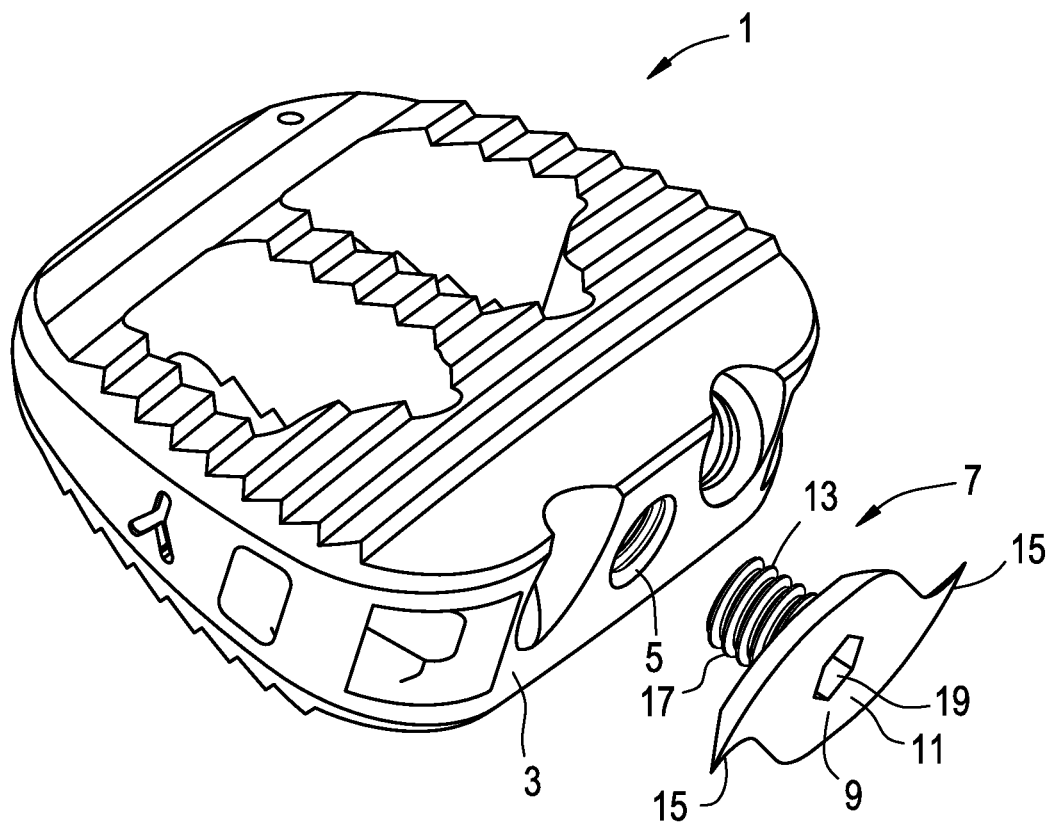
FIG. 1A discloses an exploded version of a first embodiment of the present invention (without screws) having a threaded post, wherein the bone-securing features are not in deployed position.
Figure 1B:
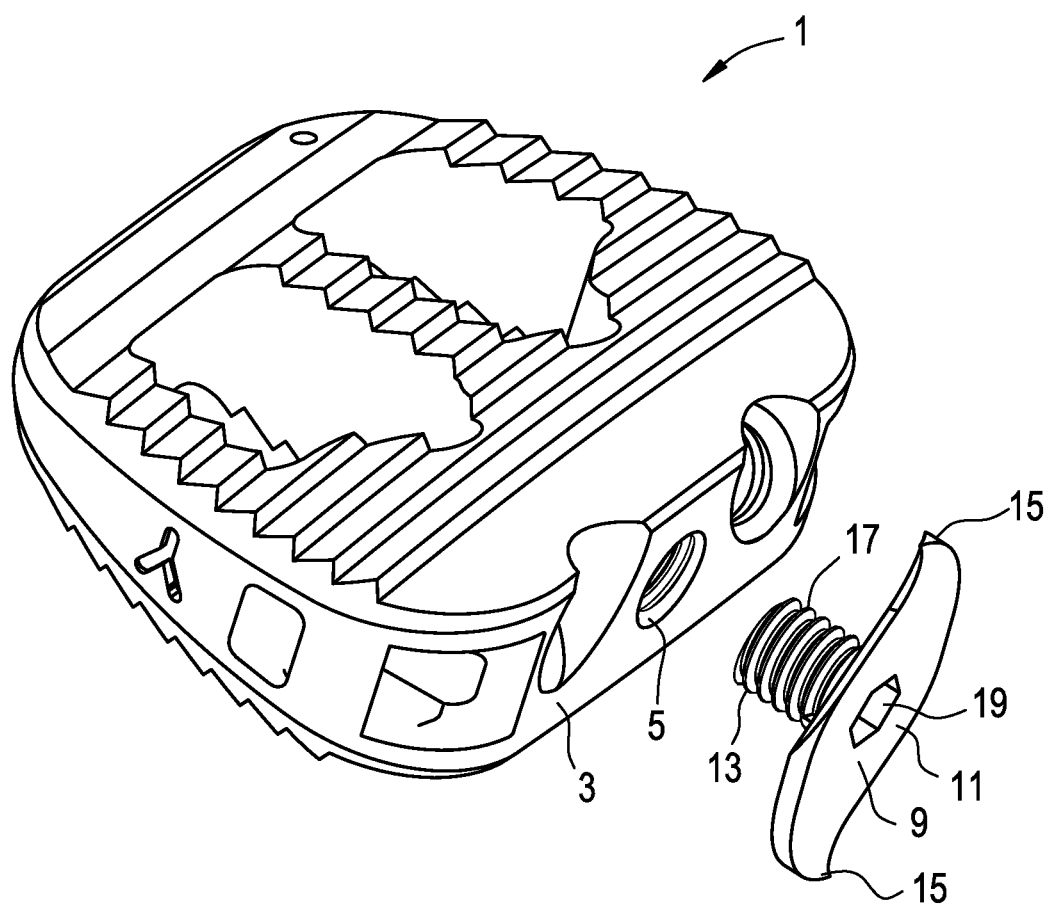
FIG. 1B discloses an exploded version of a first embodiment of the present invention (without screws) having a threaded post, wherein the bone-securing features are in deployed position.
Figure 2A:
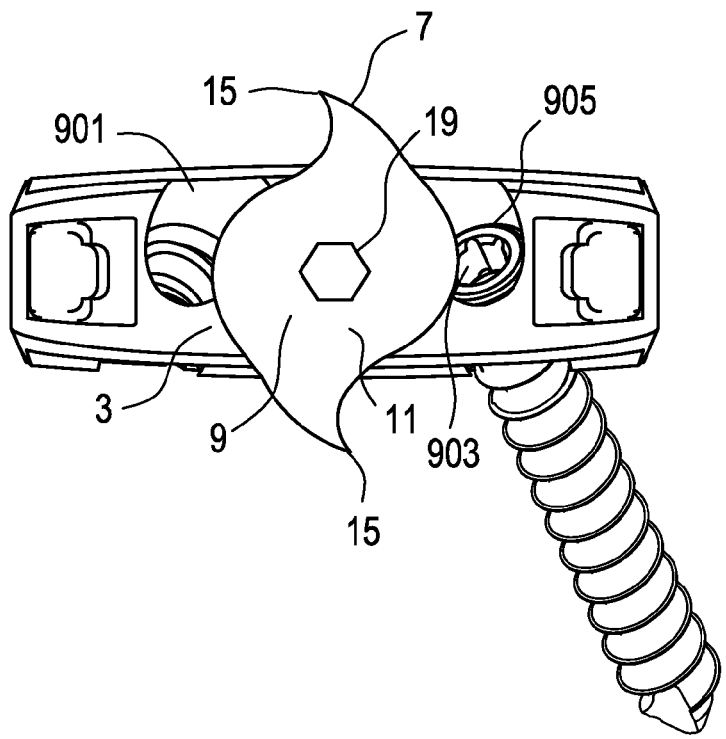
FIGS. 2A and 2B are side and top views of the assembled first embodiment of the present invention.
Figure 2B:
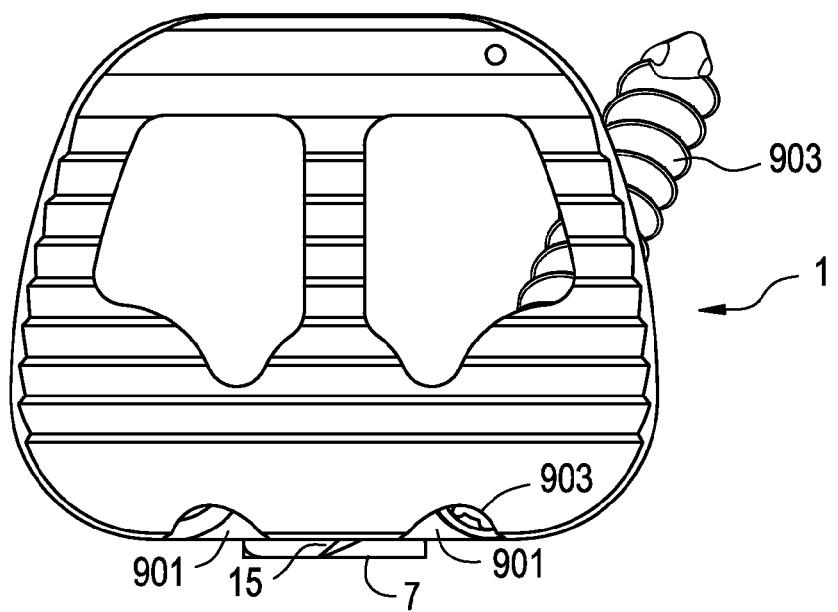

In some embodiments, as in FIG. 1A, the shaft has a threadform 17 thereon, where in other, as in FIG. 3, the shaft is unthreaded.

In some embodiments, as in FIG. 3, the bone-securing features are integral with the base portion. In others, the bone-securing features are rotatable about the base portion, as in FIG. 9.

Typically, the cover plate further comprises a recess 19 opening upon the anterior face of the base portion. Preferably, this opening has a hexagonal transverse cross-section.

In some embodiments, as in FIGS. 1A and 3, the bone-securing features extend laterally from the base portion and the shaft is rotatable with the receptacle.

Figure 6:
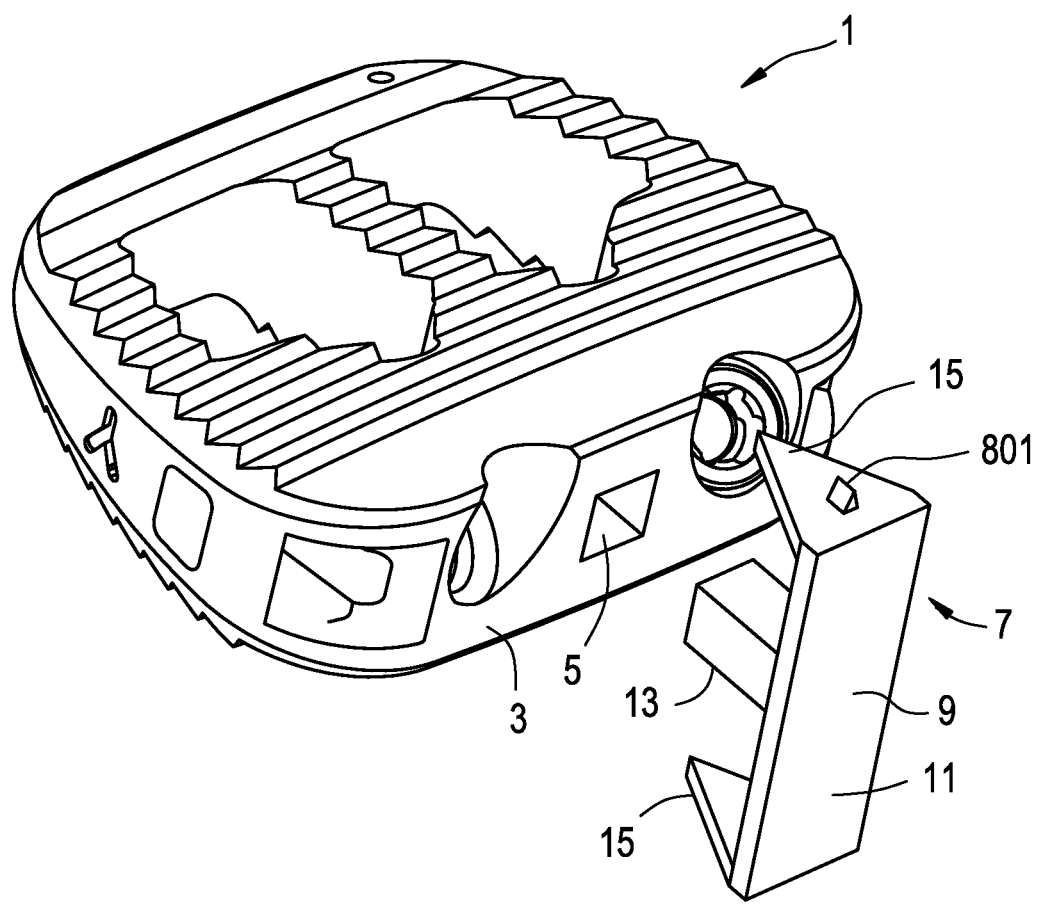
FIG. 6 discloses an exploded version of a fifth embodiment of the present invention (without screws) having a smooth rectangular post and opposed bone-securing features.

In some embodiments, as in FIG. 6, the bone-securing features extend posteriorly from the base portion.

Figure 7:
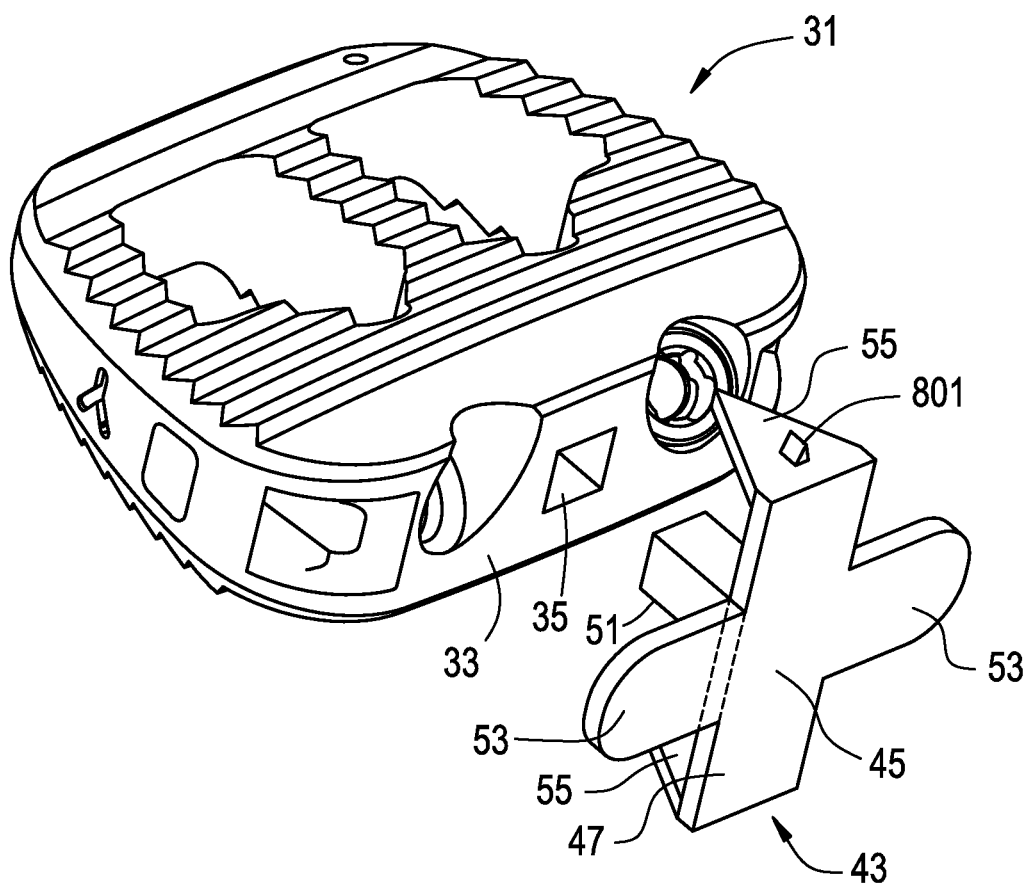
FIG. 7 discloses an exploded version of a sixth embodiment of the present invention (without screws) having a smooth rectangular post; opposed bone-securing features; and lateral flanges.

In some embodiments, as in FIGS. 6 and 7, the bone-securing features comprise an anti-backout feature 801.

The base portion of the cover plate acts as a hub for the other features of the cover plate.

The recess that opens upon the anterior face of the base portion of the cover plate functions as a receptacle for a tool that is able to rotate the cover plate. In some preferred embodiments, this recess has a hexagonal transverse cross-section, so as to be useful with standard hexagonal screwdrivers.

The purpose of the post to provide a removable engagement of the cover plate to the cage. Accordingly, the post does not preferably possess any features that would provide a permanent engagement between the cover plate and the cage, such as a snap feature.

In some embodiments the post has a smooth outer surface, as in FIG. 3. This surface is usually adopted when the bone-securement features are tapped into the bone.

In some embodiments the post has a threaded outer surface, as in FIG. 1A. This threaded surface is usually adopted when the bone-securement features are rotated into the bone.

In some embodiments the post has a circular transverse cross-section, as in FIG. 1A. This threaded surface may be usefully adopted when the bone-securement features are rotated into the bone.

In some embodiments the post has a rectangular transverse cross-section, as in FIG. 6. This surface is usually adopted when the bone-securement features are tapped into the bone. The non-circular cross section of the post provides for auto-alignment of the cover plate.

Figure 4A:
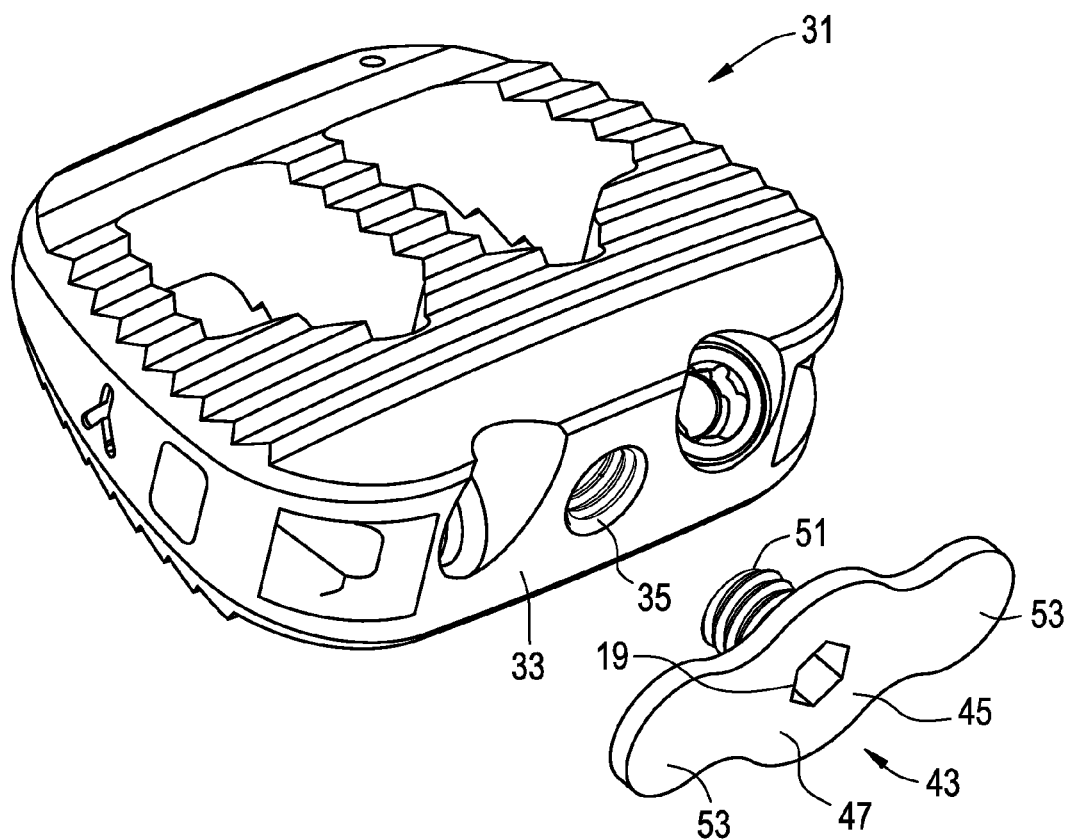
FIG. 4A discloses an exploded version of a third embodiment of the present invention (without screws) having a threaded post and lateral flanges.
Figure 4B:
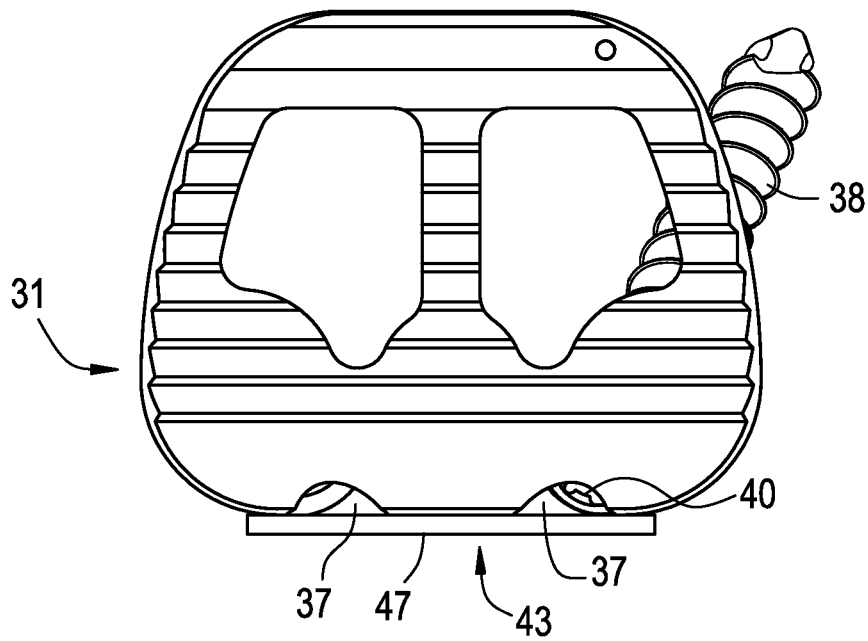
FIGS. 4B and 4C are side and top views of the assembled third embodiment of the present invention.
Figure 4C:
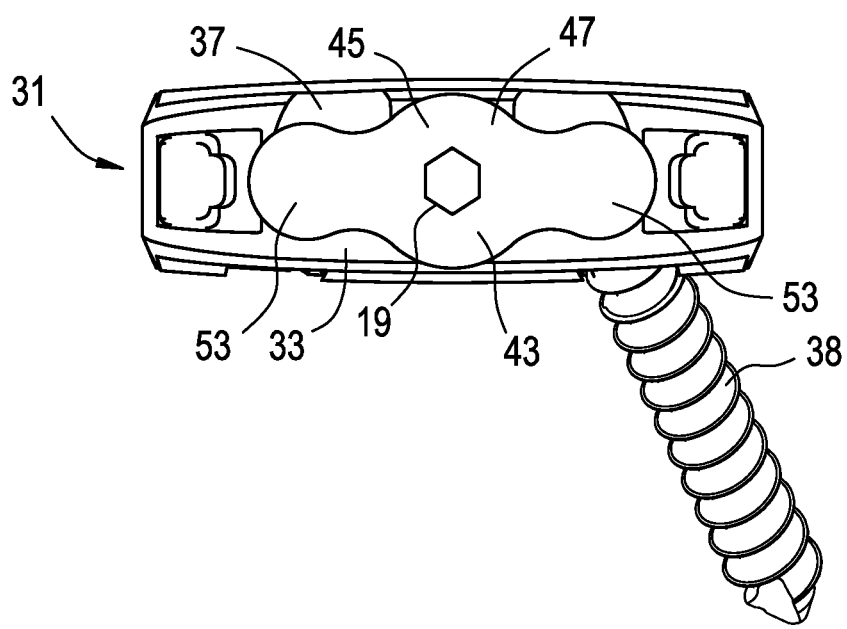
Figure 5:
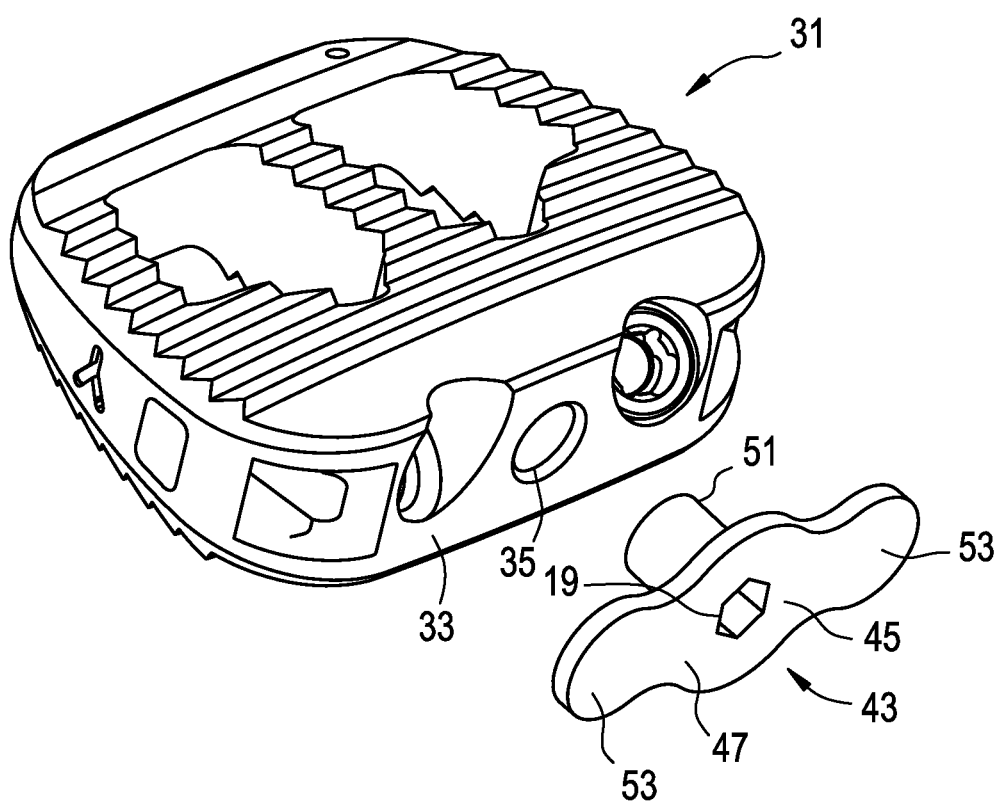
FIG. 5 discloses an exploded version of a fourth embodiment of the present invention (without screws) having a smooth post and lateral flanges.

The purpose of the flange is to provide a physical stop against the anterior movement of a screw expulsing from the cage. Because the flanges do not enter the bone, they need not have sharp features. In fact, because the implanted flanges are likely located near the aorta or vena cava of the patient's vascular system, it is preferred that the flanges consist of only smooth edges and surfaces. For example, FIG. 4 shows a pair of flanges that have only smooth surfaces.

Any feature that effectively penetrates the bone and locks the cover plate into an adjacent vertebral body can be considered a bone-securing feature. In some embodiments (as in FIG. 1A), the bone-securing feature 15 is a tooth, while in others (as in FIG. 6), it is a knife-edge 203.

In some embodiments using cover plate rotation for bone securement, the tooth extends transversely from the longitudinal axis of the base portion of the cover plate and in the same plane as the base portion, as in FIG. 1A. In some embodiments using cover plate tapping for bone securement, the knife-edge extends perpendicularly from the longitudinal axis of the base portion of the cover plate but normal to the plane of the base portion, as in FIG. 6.

In some preferred embodiments, the bone-securing feature enters the bone by first placing the post of the cover plate into the corresponding cage receptacle so that the bone securement feature is against the anterior face of a vertebral body and simply tapping the base portion of the cover plate in a posterior direction until the cover plate contacts the anterior wall of the cage. In other embodiments, the cover plate need not contact the anterior wall of the cage. This method may be used for the securement of the assembly of FIG. 6.

In other embodiments, the bone-securing feature enters the bone by first placing the post of the cover plate into the corresponding cage receptacle so that each bone securement feature is between the endplates of opposed vertebral bodies, and then rotating the cover plate until the cover plate contacts the anterior wall of the cage. This method may be used for securement of the assembly of FIG. 1A.

Now referring to FIGS. 4A-C, 5 and 7, there is provided an assembly comprising:
 a) an intervertebral fusion cage 31 positionable between adjacent vertebral bodies, the cage having an anterior face 33 having a receptacle 35 and a pair of anchor holes 37,
 b) bone anchors 38 received in the anchor holes, each anchor having a proximal head 40, and
 c) a cover plate 43 having:
  i) a base portion 45 having an anterior face 47 and a posterior face (not shown),
  ii) a post 51 extending from the posterior face of the base portion and removably engaged in the receptacle of the cage, and
  iii) opposed flanges 53 extending from the base portion, each flange located substantially anterior to a respective anchor head to prevent backout of the associated anchor.
 In some embodiments, the cover plate further comprises:
  iv) opposed bone-securing features 55 extending from the base portion, as in FIG. 7.

Figure 8:
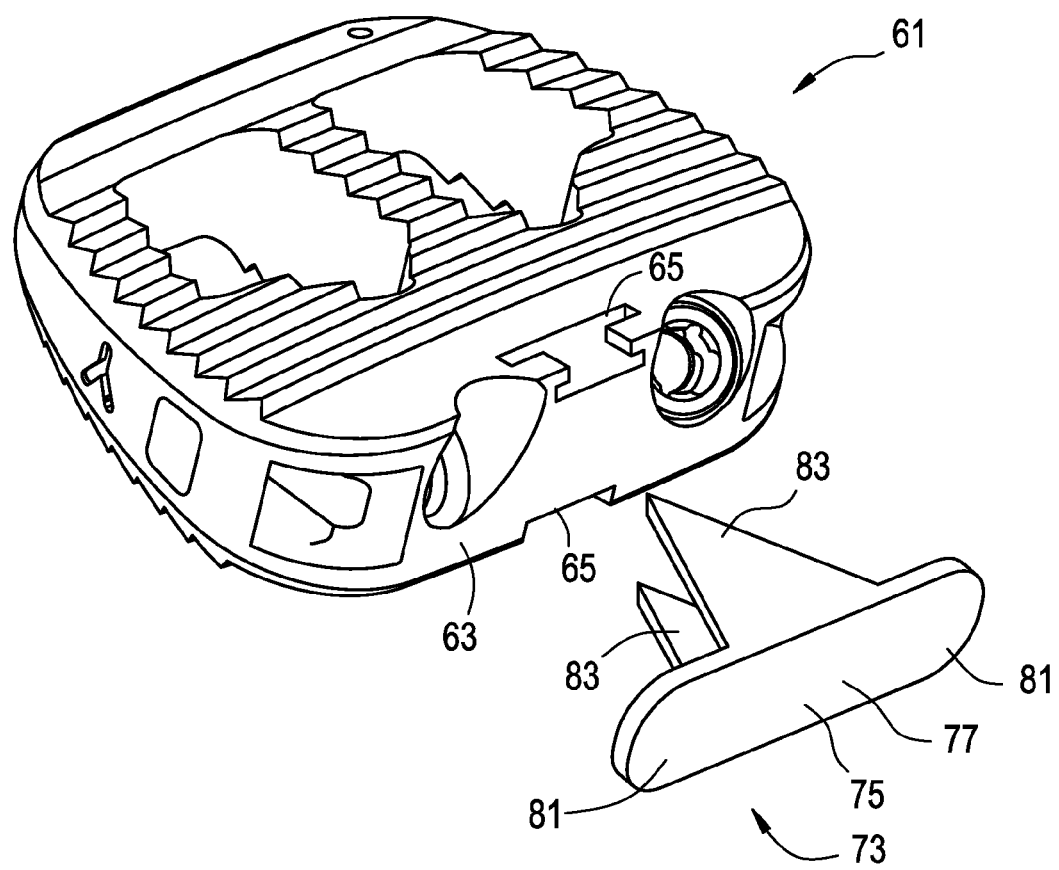
FIG. 8 discloses an exploded version of a seventh embodiment of the present invention (without screws) having opposed bone-securing features and lateral flanges.

Now referring to FIG. 8, there is provided an assembly comprising:
 a) an intervertebral fusion cage 61 positionable between adjacent vertebral bodies, the cage having an anterior face 63 having a pair of slots 65 and a pair of anchor holes 67,
 b) bone anchors (not shown) received in the screw holes, each anchor having a proximal head,
 c) a cover plate 73 having:
  i) a base portion 75 having an anterior face 77 and a posterior face (not shown),
  ii) opposed flanges 81 extending laterally from the base portion, each flange located substantially anterior to a respective anchor head to prevent backout of the respective anchor head,
  iii) opposed bone-securing features 83 extending from the base portion and passing through the respective slots.

Figure 9:
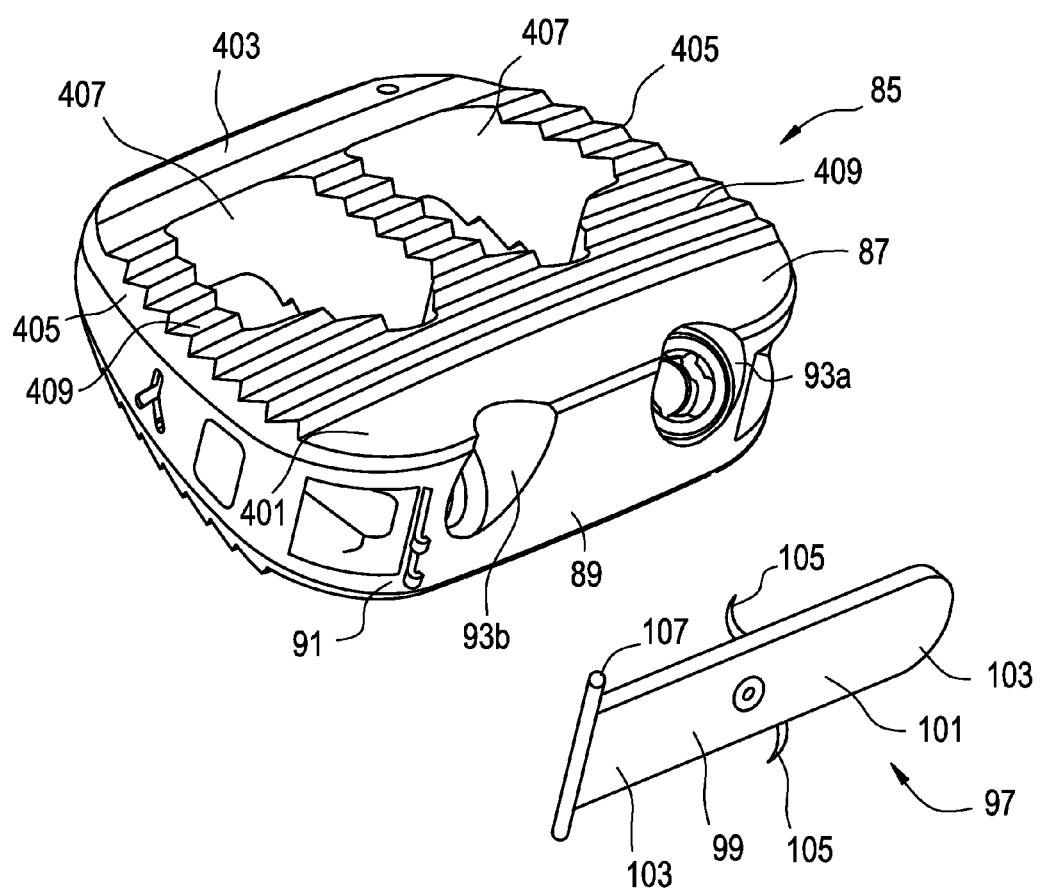
FIG. 9 discloses an exploded version of an eighth embodiment of the present invention (without screws) having bone-securing features and lateral hooks.

Now referring to FIG. 9, there is provided an assembly comprising:
 a) an intervertebral fusion cage 85 positionable between adjacent vertebral bodies, the cage having an anterior wall 87 having an anterior face 89, the anterior face having a pair of pivoting features (preferably hooks 91 extending therefrom) and a pair of anchor holes 93 extending therethrough, b) bone anchors 95 received in the anchor holes, each anchor having a proximal head,
c) a cover plate 97 having:
   i) a base portion 99 having an anterior face 101 and a posterior face (not shown),
   ii) opposed flanges 103 extending laterally from the base portion, each flange located substantially anterior to a respective screw head to prevent backout of the respective anchor head,
   iii) opposed bone-securing features 105 rotatably connected to the base portion,
   iv) a bar 107 extending from the base portion and received in the hooks.

Figure 10:
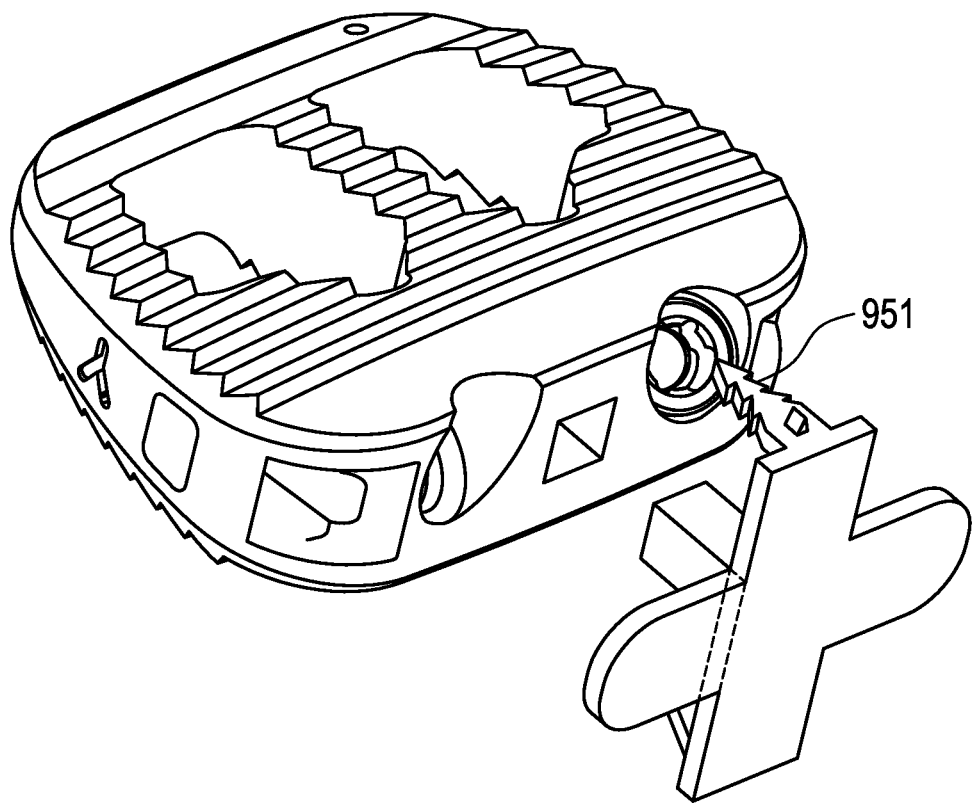
FIG. 10 discloses a cover plate in which the bone-securing features comprise barbs that provide both ease of insertion and expulsion resistance.

In some embodiments, the secondary cover plate may include features that promote ease of insertion, but would also strongly resist expulsion forces. For example, FIG. 10 discloses a cover plate in which the bone-securing features comprise barbs 951 that provide both ease of insertion and expulsion resistance. Likewise, FIGS. 6 and 7 each disclose a bone engaging feature 801 on a surface of a knife-edge, wherein the tooth extends perpendicularly to the longitudinal axis of the knife-edge. The bone engaging feature can be a tooth (as shown), a pyramid, a ridge, a keel, or a spike. This tooth provides both ease of insertion and expulsion resistance.

In addition to the anti-backout features that could be designed into the secondary cover plate, a combination of one or more of the following features could also be introduced to enhance performance: bone growth coatings (i.e., titanium calcium, phosphate, or hydroxyapatite; porous features in the bone-securing portions; anti-infection coatings; and tissue anti-adhesion coatings.

In the embodiments shown (as in FIG. 1A), the advancement of the cover plate is coupled with rotation of the cover plate. However, in other embodiments (not shown), the advancement of the cover plate is de-coupled from rotation of the cover plate. This may be accomplished by making the cover plate from two different components having separate drive features.

In general, the cage of the present invention is a stand-alone cage adapted for use in intervertebral fusions. These cages typically have screw holes through the anterior face for receiving bone screws. In some embodiments, and now referring to FIG. 9, the cage of the present invention comprises:
a) an anterior wall 87 having an anterior surface 89, an upper surface 401, a lower surface (not shown), a first throughhole 93a extending upwards from the anterior surface and a second throughhole 93b extending downwards from the anterior surface,
b) a posterior wall 403, and
c) first and second side walls 405 connecting the anterior and posterior walls.

Typically, the anterior, posterior and sidewalls of the cage define a central, vertical through-hole 407 that is adapted for promoting fusion between opposed vertebral bodies. Typically the sidewalls of such cages further comprise at least one throughhole to promote bone in-growth. Typically, the upper and lower surfaces of the cage have teeth or ridges 409 for rigidly gripping the opposed vertebral bodies. The posterior wall may have a tapered posterior surface adapted to ease insertion of the cage into the disc space. Generally, the cage may be used in either the lumbar, thoracic or cervical portions of the spine.

The bone anchors of the present invention are generally bone screws.

In one method of using the present invention, the cover plate is intended to be inserted/driven perpendicular to the proximal face of the cage in-line with the inserter. It is either delivered through a separate device or through a multi-purpose inserter that delivers the cage and then selectively allows the user to engage the cover plate. After the cage is placed and positioned per surgeon preference, a cover plate could be inserted up against a proximal face of the cage and deployed. As taught, the plate or portions of the plate penetrates the adjacent vertebral bodies either through the anterior face or from within or partially within the disc space.

In general, the cover plate, cage and bone anchors are made from metallic materials, ceramic or polymeric materials.

If a metal is chosen as the material of construction, then the metal is preferably selected from the group consisting of nitinol, titanium, titanium alloys (such as Ti-6Al-4V), chrome alloys (such as CrCo or Cr—Co—Mo) and stainless steel.

If a polymer is chosen as a material of construction, then the polymer is preferably selected from the group consisting of polycarbonates, polyesters, (particularly aromatic esters such as polyalkylene terephthalates, polyamides; polyalkenes; poly(vinyl fluoride); PTFE; polyarylethyl ketone PAEK; and mixtures thereof.

In some embodiments, the bone screws are made of a stainless steel alloy, preferably BioDur® CCM Plus® Alloy available from Carpenter Specialty Alloys, Carpenter Technology Corporation of Wyomissing, Pa. In some embodiments, the cage is made from a composite comprising carbon fiber. Composites comprising carbon fiber are advantageous in that they typically have a strength and stiffness that is superior to neat polymer materials such as a polyarylethyl ketone PAEK. In some embodiments, the cage is made from a polymer composite such as a PEKK-carbon fiber composite.

Preferably, the composite comprising carbon fiber further comprises a polymer. Preferably, the polymer is a polyarylethyl ketone (PAEK). More preferably, the PAEK is selected from the group consisting of polyetherether ketone (PEEK), polyether ketone ketone (PEKK) and polyether ketone (PEK). In preferred embodiments, the PAEK is PEEK.

In some embodiments, the cage is made from a neat polymer without any carbon fiber additive. Preferably, the polymer is a polyarylethyl ketone (PAEK), more preferably PEEK.

In some embodiments, the carbon fiber comprises between 1 vol % and 60 vol % (more preferably, between 10 vol % and 50 vol %) of the composite. In some embodiments, the polymer and carbon fibers are homogeneously mixed. In others, the material is a laminate. In some embodiments, the carbon fiber is present in a chopped state. Preferably, the chopped carbon fibers have a median length of between 1 mm and 12 mm, more preferably between 4.5 mm and 7.5 mm. In some embodiments, the carbon fiber is present as continuous strands.

In especially preferred embodiments, the composite comprises:
a) 40-99% (more preferably, 60-80 vol %) polyarylethyl ketone (PAEK), and
b) 1-60% (more preferably, 20-40 vol %) carbon fiber,
wherein the polyarylethyl ketone (PAEK) is selected from the group consisting of polyetherether ketone (PEEK), polyether ketone ketone (PEKK) and polyether ketone (PEK).

In some embodiments, the composite consists essentially of PAEK and carbon fiber. More preferably, the composite comprises 60-80 wt % PAEK and 20-40 wt % carbon fiber. Still more preferably the composite comprises 65-75 wt % PAEK and 25-35 wt % carbon fiber.

I claim:

1. An assembly comprising:
   a) an intervertebral fusion cage positionable between adjacent vertebral bodies, the cage having an anterior wall having an anterior face, the anterior face having a pair of pivoting features and a pair of anchor holes extending therethrough,
   b) bone anchors received in the anchor holes, each anchor having a proximal head,
   c) a cover plate having:
      i) a base portion having an anterior face and a posterior face,
      ii) opposed flanges extending laterally from and forming part of the base portion, each flange located substantially anterior to the respective bone anchor head to prevent backout of the respective anchor head,
      iii) opposed bone-securing features rotatably connected to the base portion,
      iv) a bar extending from the base portion and received in the pivoting features,
   wherein the opposed bone-securing features extend above and below the base portion.

2. An assembly comprising:
   a) an intervertebral fusion cage positionable between adjacent vertebral bodies, the cage having an anterior face having a pair of anchor holes extending therethrough and an uppermost upper surface,
   b) bone anchors received in the anchor holes, each anchor having a proximal head,
   c) a cover plate having:
      i) a base portion having an anterior face and a posterior face,
      ii) opposed bone-securing features rotatably extending from the base portion,
   wherein the cover plate is removably connected to the cage, wherein the cover plate extends above the uppermost upper surface of the cage.

3. The assembly of claim 2 wherein the cover plate further comprises:
   iii) opposed flanges extending laterally from the base portion, each flange located substantially anterior to a respective anchor head to prevent backout of the respective anchor head.

4. The assembly of claim 2 wherein the coverplate is slidably connected to the cage.

* * * * *